United States Patent [19]

Genzer et al.

[11] 4,024,136

[45] * May 17, 1977

[54] PROCESS FOR THE PREPARATION OF 4-HYDROXY-3-(5-METHYL-3-ISOXAZOLYLCARBAMOYL)-2-METHYL-2H-1,2-BENZOTHIAZINE 1,1-DIOXIDE

[75] Inventors: Jerome Daniel Genzer, Livingston; Francisco Carrio Fontsere, Andover, both of N.J.

[73] Assignee: Warner-Lambert Company, Morris Plains, N.J.

[ * ] Notice: The portion of the term of this patent subsequent to June 1, 1993, has been disclaimed.

[22] Filed: Mar. 10, 1976

[21] Appl. No.: 665,485

Related U.S. Application Data

[63] Continuation-in-part of Ser. No. 588,752, June 20, 1975, Pat. No. 3,960,856.

[52] U.S. Cl. .............................. 260/243 R; 424/246
[51] Int. Cl.² ....................................... C07D 279/02
[58] Field of Search ............................... 260/243 R

[56] References Cited

UNITED STATES PATENTS 3,822,258   7/1974   Zinnes et al. ..................... 260/243

*Primary Examiner*—John M. Ford
*Attorney, Agent, or Firm*—Albert H. Graddis; Frank S. Chow; Anne M. Kelly

[57] ABSTRACT

An improved process for the preparation of 4-hydroxy-3-(5-methyl-3-isoxazolylcarbamoyl)-2-methyl-2H-1,2-benzothiazine 1,1-dioxide (I), a known anti-inflammatory agent, is described. The process involves the reaction of a solution of alkyl 2,3-dihydro-3-oxo-1,2-benzisothiazole-2-acetate 1,1-dioxide (II) in dimethylformamide, with an alkali metal alkoxide using the specific portions of reactants and carefully controlled reaction conditions. Acidification of the reaction mixture precipitates out alkyl 4-hydroxy-2H-1,2-benzothiazine-3-carboxylate 1,1-dioxide (III) in substantially pure form in high yields, without recrystallization. Product III is methylated on the sulfonamide nitrogen and reacted with 3-amino-5-methylisoxazole to obtain crude I. A further improvement in the process of the invention involves a more efficient method for purifying crude product I by solubilizing in dimethylformamide with heating to 125° C. to 148° C. The hot solution is filtered, and the filtrate is cooled to obtain crystalline product I.

8 Claims, No Drawings

PROCESS FOR THE PREPARATION OF 4-HYDROXY-3-(5-METHYL-3-ISOXAZOLYLCARBAMOYL)-2-METHYL-2H-1,2-BENZOTHIAZINE 1,1-DIOXIDE

CROSS REFERENCE TO RELATED APPLICATIONS

This application is a continuation-in-part of U.S. Ser. No. 588,752, filed June 20, 1975, now U.S. Pat. No. 3,960,856, issued June 1, 1976.

BACKGROUND OF THE INVENTION

1. Field of the Invention

The present invention relates to an improved process for the preparation of 4-hydroxy-3-(5-methyl-3-isoxazolylcarbamoyl)-2-methyl-2H-1,2-benzothiazine 1,1-dioxide (I).

2. Description of the Prior Art

The preparation of 4-hydroxy-3-(5-methyl-3-isoxazolylcarbamoyl)-2-methyl-2H-1,2-benzothiazine 1,1-dioxide (I) has been described by Zinnes et al. in U.S. Pat. NO. 3,822,258. Other novel routes to its preparation have also been described by Sircar et al. in U.S. Pat. No. 2,821,211 and by Lombardino in U.S. Pat. No. 3,853,862. The following intermediates of interest in the process of this invention:

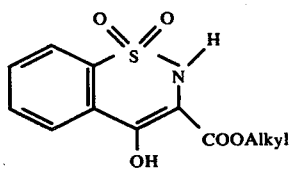

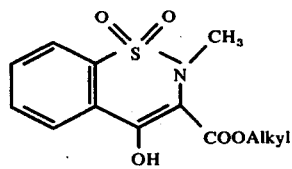

have been disclosed in U.S. Pat. No. 3,501,466 and U.S. Pat. No. 3,591,584 and by Lombardino et al., J. Med. Chem. 14: 173 (1971). These intermediates were used by Zinnes in U.S. Pat. No. 3,822,258 for the preparation of the subject compound (I) and by Lombardino in U.S. Pat. No. 3,591,584 for the preparation of related benzothiazine amides, useful as anti-inflammatory agents.

DESCRIPTION OF THE PARTICULAR EMBODIMENTS

According to the present invention, an improved process for the production of 4-hydroxy-3-(5-methyl-3-isoxazolylcarbamoyl)-2-methyl-2H-1,2-benzothiazine 1,1-dioxide (I):

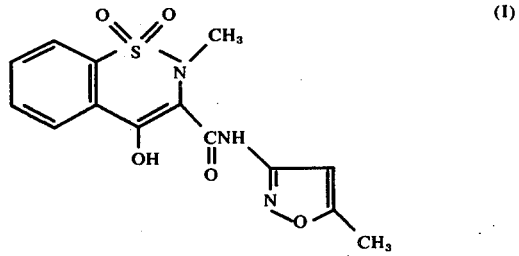

involves a multi-step procedure wherein, in an improved initial reaction step, a suspension of an alkali metal alkoxide of a lower alcohol in dimethylformamide is combined, with stirring, with a solution of compound II:

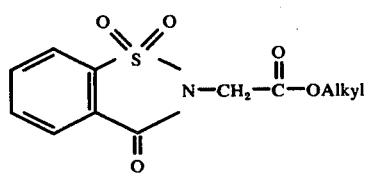

Alkyl 2,3-dihydro-3-oxo-1,2-benzisothiazole-2-acetate 1,1-dioxide (II)

in dimethylformamide, as rapidly as possible while maintaining the internal reaction temperature between 15° C. to 30° C. Preferably, the solution of II is added to the suspension of the alkali metal alkoxide in dimethylformamide. More than two but less than six moles of the alkoxide are used for each mole of the alkyl 2,3-dihydro-3-oxo-1,2-benzisothiazole-2-acetate 1,1-dioxide (II). The compound II alkyl ester may be a 1 to 7 carbon lower alkyl ester, and in order to achieve optimum yields in this improved initial reaction step, the alkyl group in the alkoxide reagent must correspond to the compound II alkyl ester.

After the combination of reactants has been completed, stirring is continued for a specific period of time. Upon completion of reaction time, the reaction mixture is acidified. The total time from the initial combination of reactants to acidification should be from about 20 to about 60 minutes, preferably from about 30 minutes to about 50 minutes. Acidification of the reaction mixture with a dilute mineral acid precipitates out compound III:

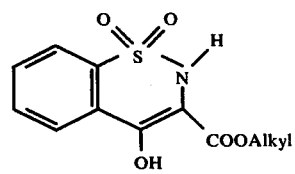

Alkyl 4-hydroxy-2H-1,2-benzothiazine-3-carboxylate 1,1-dioxide (III)

The compound III alkyl ester is a 1 to 7 carbon atom lower alkyl ester, corresponding to the compound II alkyl ester. Compound III is obtained in substantially pure form and in high yield, without the need for recrystallization according to the improved initial reaction process of this invention. Yields in the range of 72 to 82% are obtained and compound III may be used directly in subsequent reaction steps leading to the preparation of compound I.

It should be noted that, in contrast to the statement made in the prior art (J. Med. Chem. 14: 173, 1971), the yield in the above-described reaction, when carried out in the dimethylformamide solvent, is consistently high. Quite surprisingly, it has been found that the improved initial reaction step of this invention may be performed in dimethylformamide in a reproducible manner which is easily adapted to large scale production techniques. Additionally, the yield and purity of compound III prepared according to the improved initial reaction step of this invention is significantly higher than has been previously reported for other reaction conditions. Thus, the reaction conditions described above are critical: higher temperatures, the use of mole ratios outside the stated ranges or the extension of reaction and stirring times have been found to significantly reduce the purity of the product obtained as well as to lower the overall yield of compound III.

As has been stated above, the substantially pure form of compound III obtained according to the improved initial reaction step of this invention is subsequently subjected to additional reactions to obtain the desired compound I. For example, a conventional methylation reaction is conducted at about 25° C. using a suitable methylating agent, such as dimethylsulfate and sodium hydroxide in either an aqueous lower alcohol solution or in dimethylformamide, to obtain compound IV:

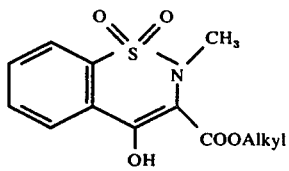

Alkyl 4-hydroxy-2-methyl-
2H-1,2-benzothiazine-3-
carboxylate 1,1-dioxide (IV)

Again, the alkyl group in compound IV may be a 1 to 7 carbon atom lower alkyl group corresponding to the compound III alkyl ester.

The final step in the preparation of compound I is carried out in a manner similar to that described by Zinnes in U.S. Pat. No. 3,822,258, i.e., reaction with 3-amino-5-methylisoxazole in a xylene solvent. However, according to the process of this invention, it has been found that the use of a molecular sieve is unnecessary. Instead, the xylene solution of compound IV and 3-amino-5-methylisoxazole are refluxed for about 13–18 hours. In a preferred refluxing procedure, about 3 to 4% of the xylene solvent is distilled off periodically and replaced with fresh xylene at about 4 hour intervals. When refluxing has been completed, the reaction mixture is cooled and filtered to obtain crude product I. According to prior art procedures, crude product I must be recrystallized from large amounts of dioxane solvent in order to obtain pure product I. It has now been found, according to an improved final reaction step of this invention, that crude product I can be purified with high recovery (about 80%) by recrystallization from a hot dimethylformamide solution. Large amounts of dioxane solvent are not required.

According to the improved final reaction step of this invention, crude product I is heated in from about 4 to about 8 volumes of dimethylformamide, to a temperature of from about 125° to about 148° C to achieve complete dissolution. Preferably, crude product I is heated in about 6 volumes of dimethylformamide to a temperature of about 127° C to achieve complete dissolution. The hot solution is filtered and the filtrate obtained is cooled to from about 5° to about 10° C for a time sufficient to allow substantially all of product I to crystallize out of solution (typically, for approximately 1 hour). After filtering and washing with small amounts of dimethylformamide (room temperature), followed by washing with proprietary alcohol and drying, substantially pure 4-hydroxy-3-(5-methyl-3-isoxazolylcarbamoyl)-2-methyl-2H-1,2-benzothiazine 1,1-dioxide (I) in good yield is obtained.

The above purification procedure eliminates the need for large volumes of costly, hazardous dioxane solvent which was required in the prior art recrystallization purification process. Thus, the improved multistep process of this invention for preparing 3-(5-methyl-3-isoxazolylcarbamoyl)-2-methyl-2H-1,2-benzothiazine 1,1-dioxide (I), a useful antiinflammatory agent, provides a substantial advantage over previously described methods and permits large scale production of this product much more economically.

An additional feature of this invention resides in the fact that the improved initial reaction step, wherein alkyl 2,3-dihydro-3-oxo-1,2-benzisothiazole-2-acetate 1,1-dioxide (II) is rearranged to form alkyl 4-hydroxy-2H-1,2-benzothiazine-3-carboxylate 1,1-dioxide (III) may be used with particular advantage for the preparation of known benzothiazine amides and related derivatives, which are useful anti-inflammatory agents.

In order to further illustrate this invention, the following examples are provided:

EXAMPLE 1

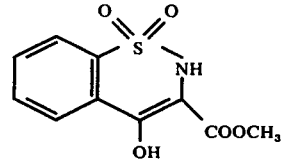

Preparation of Methyl
4-Hydroxy-2H-1,2-Benzothiazine-3-Carboxylate
1,1-Dioxide

In a nitrogen atmosphere, a solution of 30 grams (0.117 moles) of methyl-2,3-dihydro-3-oxo-1,2-benzisothiazoline-2-acetate 1,1-dioxide in 50 ml DMF is added, with stirring, to a suspension of 18.9 grams (0.351 moles) of sodium methoxide in 100 ml DMF over a period of about 5 minutes and the internal temperature is maintained at 15°–30° C. by means of an ice bath. The stirring is continued for 30 minutes at about 30° C. after the completion of the addition. With external cooling, a solution of 35 ml concentrated HCl in 600 ml of water is added, maintaining the internal temperature below 35° C. After this addition, the mixture is cooled to 10° C. and filtered. The filter cake is washed thoroughly with water and the product is dried. Yield is 23.5 grams (78.2%) m.p. 173°–175° C. The total addition and stirring time prior to acidification should be less than 1 hour. For example, if the addition should take 30 minutes the batch should be stirred only an additional 15–20 minutes.

EXAMPLE 2

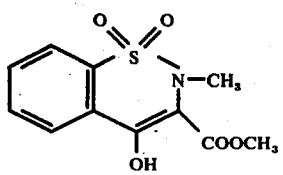

Preparation of Methyl 4-Hydroxy-2-Methyl-2H-1,2-Benzothiazine-3-Carboxylate 1,1-Dioxide To a suspension of 3.5 grams (.086 moles) of sodium hydroxide in 68 ml DMF, a solution of 20 grams (.078 moles) of methyl 4-hydroxy-2H-1,2-benzothiazine-3-carboxylate 1,1-dioxide is added in 34 ml DMF over a period of about 5 minutes at about 25° C. 11.9 Grams (.094 moles) of dimethyl sulphate is added over a period of about 30 minutes at a maximum temperature of 30° C. The reaction is stirred for 3 hours at 30° C. and diluted with about 150 ml of water. It is cooled to 15° C., filtered and washed well with water. After drying, there is obtained 20 grams (95%) of product, m.p. 163°–165° C.

EXAMPLE 3

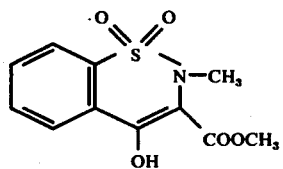

Methyl 4-Hydroxy-2-Methyl-2H-1,2-Benzothiazine-3-Carboxylate-1,1-Dioxide

To a suspension of 90 grams (0.352 moles) of methyl 4-hydroxy-2H-1,2-benzothiazine-3-carboxylate 1,1-dioxide in 450 ml proprietory alcohol there is added a solution of 15.5 grams (0.3875 moles) of sodium hydroxide in 450 ml of water at a temperature of less than 20° C. 53.4 Grams (0.423 moles) of dimethyl sulphate is added while stirring, at 25° C. and the mixture is then allowed to stir for about 15 hours. It is cooled to 10° C. and filtered. The cake is washed with water, followed by a 50% alcohol/water wash, and dried. Yield is 90 grams (95%) m.p. 162.5°–164° C.

EXAMPLE 4

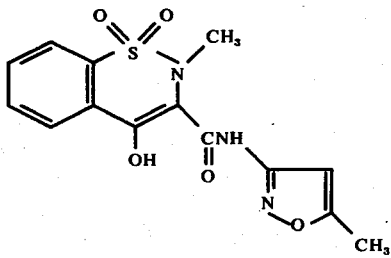

4-Hydroxy-3-(5-Methyl-3-Isoxazolylcarbamoyl)-2-Methyl-2H-1,2-Benzothiazine 1,1-Dioxide To an appropriate flask equipped for reflux and/or distillation, 900 ml xylene, 40 grams (.149 moles) methyl 4-hydroxy-2-methyl-2H-1,2-benzothiazine-3-carboxylate 1,1-dioxide and 19.94 grams (.203 moles) of 3-amino-5-methylisoxazole are added. The mixture is refluxed for 13–18 hours. At one hour intervals, about 3–4% of the solvent volume is distilled off. Every 4 to 5 hours fresh xylene is added, equal in amount to that distilled during this period. At the end of the heating period, the reaction is cooled to 25° C., filtered and the cake is washed with xylene. After drying, the crude product weighed 43.8 grams (88%). This material could be recrystallized from about 40–50 volumes of dioxane with an 80–85% recovery of acceptable material. An alternate procedure for the purification of crude product is as follows:

EXAMPLE 5

Purification of Crude 4-Hydroxy-3-(5-Methyl-3-Isoxazolylcarbamoyl-2-Methyl-2H-1,2-Benzothiazine 1,1-Dioxide 60 ml dimethylformamide is heated to about 115° C and 10 g. crude product from Example 4 is added. Heating is continued until the solid is completely dissolved (temperature about 127° C). The hot solution is filtered and the filtrate is cooled to about 5° C for 1 hour. The solids are filtered and the cake on the pad is washed with about 10 ml dimethylformamide followed by two washes with 10 ml Proprietary Solvent No. 3 ("Solox," proprietary alcohol). The product is dried at 50°–55° C atmospherically. Recovery 7.5–8 g. (75–80%). The product obtained is of higher purity than the material obtained by the re-precipitation purification described in Example 5 of U.S. Ser. No. 588,752, filed June 20, 1975, now U.S. Pat. No. 3,960,856, issued June 1, 1976.

We claim:
1. An improved process for preparing 4-hydroxy-3-(5-methyl-3-isoxazolylcarbamoyl)-2-methyl-2H-1,2-benzothiazine 1,1-dioxide (I) which comprises the following steps:
   A. suspending more than two but less than six moles of an alkali metal alkoxide of a lower alcohol in dimethylformamide;
   B. dissolving one mole of alkyl 2,3-dihydro-3-oxo-1,2-benzisothiazole-2-acetate 1,1-dioxide (II) in dimethylformamide;
   C. combining the suspension of (A) and the solution of (B) rapidly, with stirring, while maintaining the internal reaction temperature at from about 15° to about 30° C.;
   D. continuing the stirring of the reaction mixture of (C) and then acidifying, with the total time from initial reactant combination to acidification being from about 20 minutes to about 60 minutes;
   E. precipitating from (D) substantially pure alkyl 4-hydroxy-2H-1,2-benzothiazine-3-carboxylate 1,1-dioxide (III) in high yield without recrystallization;
   F. methylating the precipitrate of (E) on the sulfonamide nitrogen;
   G. refluxing the alkyl 4-hydroxy-2-methyl-2H-1,2-benzothiazine-3-carboxylate 1,1-dioxide (IV) obtained in (F) with 3-amino-5-methylisoxazole in an inert solvent to obtain crude 4-hydroxy-3-(5-methyl-3-isoxazolylcarbamoyl-2-methyl-2H-1,2-benzothiazine 1,1-dioxide (I);

H. adding crude compound I to from about 4 to 8 volumes of heated dimethylformamide;

I. heating (H) to from about 125° C to about 148° C until crude product I is completely dissolved;

J. filtering the hot solution of (I) and cooling the filtrate obtained to from about 5° C to about 10° C for a time sufficient to allow substantially all product I to crystallize out of solution; and K. filtering (J), followed by washing and drying to obtain substantially pure crystalline product I.

2. A process according to claim 1 wherein, in Step A, about 3 moles of sodium methoxide are used; and in Step B, about 1 mole of methyl 2,3-dihydro-3-oxo-1,2-benzisothiazole-2-acetate 1,1-dioxide is used.

3. A process according to claim 1 wherein, in Step D, the total reaction time prior to acidification is from about 30 minutes to about 50 minutes.

4. A process according to claim 1, wherein, in Step G, the inert solvent is xylene.

5. A process according to claim 1 wherein, in Step H, crude product I is added to about 6 volumes of heated dimethylformamide.

6. A process according to claim 1 wherein, in Step I, the heating is conducted at about 127° C to dissolve crude product I.

7. A process according to claim 1 wherein, in Step J, the cooling is conducted at about 5° C for about 1 hour to allow substantially all product I to crystallize out of solution.

8. An improved process for preparing 4-hydroxy-3-(5-methyl-2-isoxazolylcarbamoyl)-2-methyl-2H-1,2-benzothiazine 1,1-dioxide (I) which comprises the following steps:

A. suspending about 3 moles of sodium methoxide in dimethylformamide;

B. dissolving 1 mole of methyl 2,3-dihydro-3-oxo-1,2-benzisothiazole-2-acetate 1,1-dioxide in dimethylformamide;

C. combining the suspension of (A) and the solution of (B) rapidly, with stirring, while maintaining the internal reaction temperature at from about 15° C to about 30° C;

D. continuing the stirring of the reaction mixture of (C) and then acidifying, with the total time from initial reactant combination to acidification being from about 30 minutes to about 50 minutes;

E. acidifying the reaction mixture of (D) to precipitate out substantially pure methyl 4-hydroxy-2H-1,2-benzothiazine-3-carboxylate 1,1-dioxide in high yield without recrystallization;

F. methylating the precipitate of (E) on the sulfonamide nitrogen to obtain methyl 4-hydroxy-2-methyl-2H-1,2-benzothiazine-3-carboxylate 1,1-dioxide;

G. refluxing the product of (F) with 3-amino-5-methylisoxazole in xylene to obtain crude 4-hydroxy-3-(5-methyl-3-isoxazolylcarbamoyl)-2-methyl-2H-1,2-benzothiazine 1,1-dioxide (I);

H. adding crude compound I to from about 6 volumes of heated dimethylformamide;

I. heating (H) to about 127° C until crude product I is completely dissolved;

J. filtering the hot solution of (I) and cooling the filtrate obtained to about 5° C for about 1 hour to allow substantially all product I to crystallize out of solution; and K. filtering (J), followed by washing and drying to obtain substantially pure crystalline product I.

* * * * *